United States Patent [19]
Tsunakawa et al.

[11] Patent Number: 5,919,671
[45] Date of Patent: Jul. 6, 1999

[54] ANTITUMOR ANTIBIOTIC BMS-199687

[75] Inventors: Mitsuaki Tsunakawa, Kanagawa, Japan; Li-Ping Chang, New Britain, Conn.; Stephen W. Mamber, Wethersfield, Conn.; Isia Bursuker, Cheshire, Conn.; Robert Hugill, Middletown, Conn.

[73] Assignee: Bristol-Myers Squibb Company, Princeton, N.J.

[21] Appl. No.: 09/023,779

[22] Filed: Feb. 13, 1998

Related U.S. Application Data

[62] Division of application No. 08/838,223, Apr. 2, 1997, Pat. No. 5,811,440
[60] Provisional application No. 60/015,800, Apr. 17, 1996.
[51] Int. Cl.⁶ .............................. C12P 17/16; C12N 1/20
[52] U.S. Cl. .................. 435/118; 435/252.1; 435/825
[58] Field of Search ................................ 435/118, 252.1, 435/825

[56] References Cited

FOREIGN PATENT DOCUMENTS 06306074A  2/1993  Japan .

OTHER PUBLICATIONS

G.A. Snow, et al, "Chemical and Biological Properties of Mycobactins Isolated From Various Mycobacteria," Biochem. J., 115, pp. 1031–1045 (1969).

I. Bursuker, et al, Production of Interferon–γ by In Vivo Tumor–Sensitized T Cells: Association with Active Antitumor Immunity, Journal of Interferon Research, 10, pp. 1–11 (1990).

E. Borenfreund, et al, A Simple Quantitative Procedure Using Monolayer Cultures for Cytotoxicity Assays (HTD/NR–90), J. Tissue Culture Methods, 9, pp. 7–9 (1984).

W. C. Rose, "Evaluation of Madison 109 Lung Carcinoma as a Model for Screening Antitumor Drugs," Cancer Treatment Reports, 65, No. 3–4, pp. 299–312 (1981).

*Primary Examiner*—Herbert J. Lilling
*Attorney, Agent, or Firm*—David M. Morse

[57] ABSTRACT

The present invention relates to the novel antitumor antibiotic designated BMS-199687 and to its preparation. The compound is obtained by culturing a new strain of *Actinomadura ferruginea*. BMS-199687 demonstrates antitumor activity in standard antitumor animal model systems.

3 Claims, 4 Drawing Sheets

ANTITUMOR ANTIBIOTIC BMS-199687

CROSS-REFERENCE TO RELATED APPLICATION(S)

This is a Divisional of U.S. Ser. No. 08/838,223, filed Apr. 2, 1997, now U.S. Pat. No. 5,811,440, which claims the benefit of Provisional Application No. 60/015,800 filed Apr. 17, 1996.

BACKGROUND OF THE INVENTION

1. Field of the Invention

The present invention relates to a novel antibiotic designated herein as BMS-199687, a process for preparing the antibiotic by fermentation of a new strain of *Actinomadura ferruginea* and to the use of the antibiotic as an antitumor agent.

2. Description of the Prior Art

The antibiotic BMS-199687 is classified by the *CRC Handbook of Antibiotic Compounds* as a member of the mycobactin class of antibiotics. Other examples of mycobactins have been reported (see, for example, *Biochem. J.* 115:1031–1045, 1969), but the known mycobactins differ substantially in structure from BMS-199687.

Published Japanese Patent Application JP 06306074A discloses mycobactin antibiotics designated BE-32030 produced by Nocardia sp. A32030 (FERM P-13395) which are reported to have antitumor activity.

SUMMARY OF THE INVENTION

Figure 1:
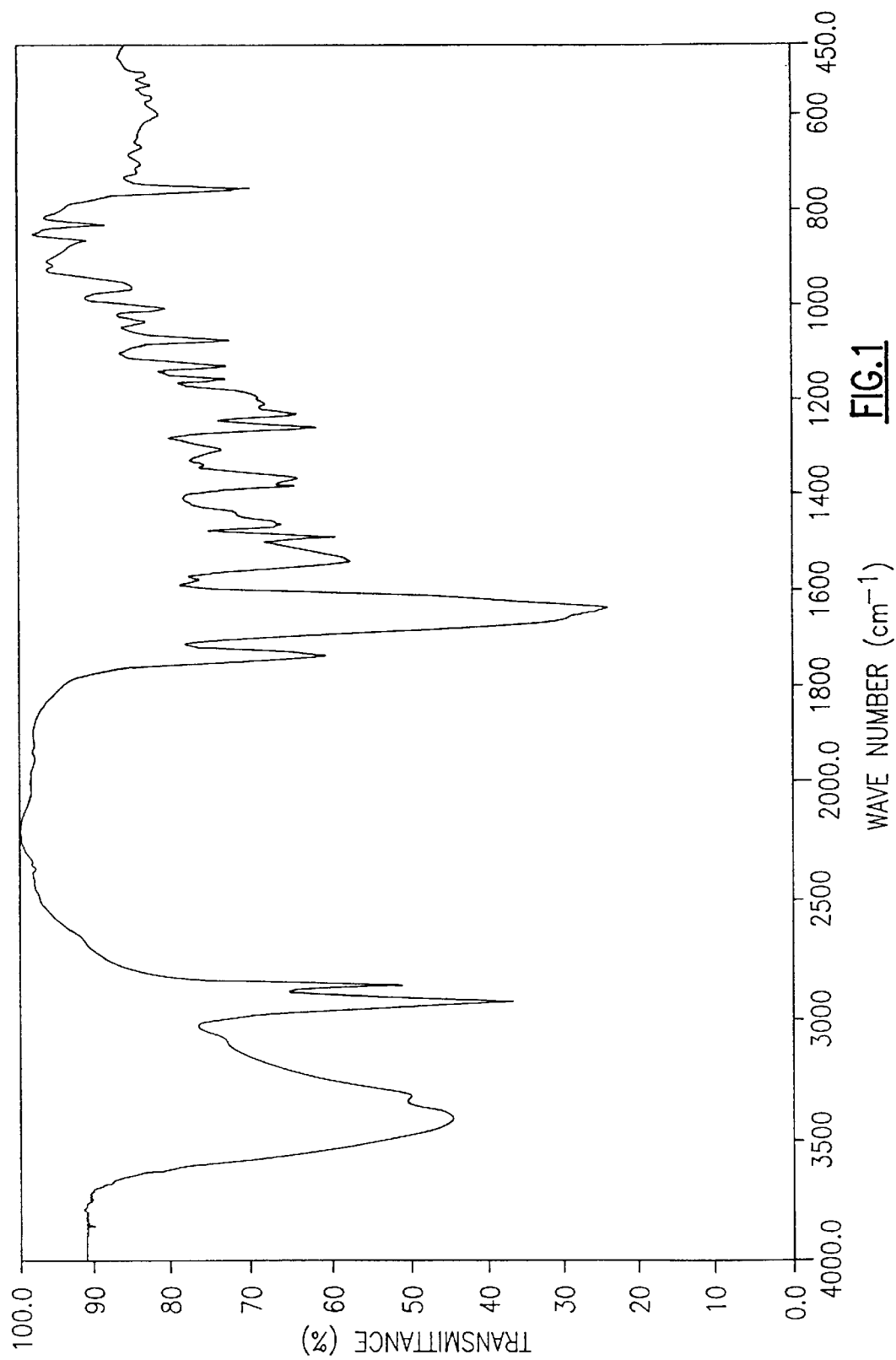
FIG. 1 shows the IR spectrum of BMS-199687.
Figure 2:
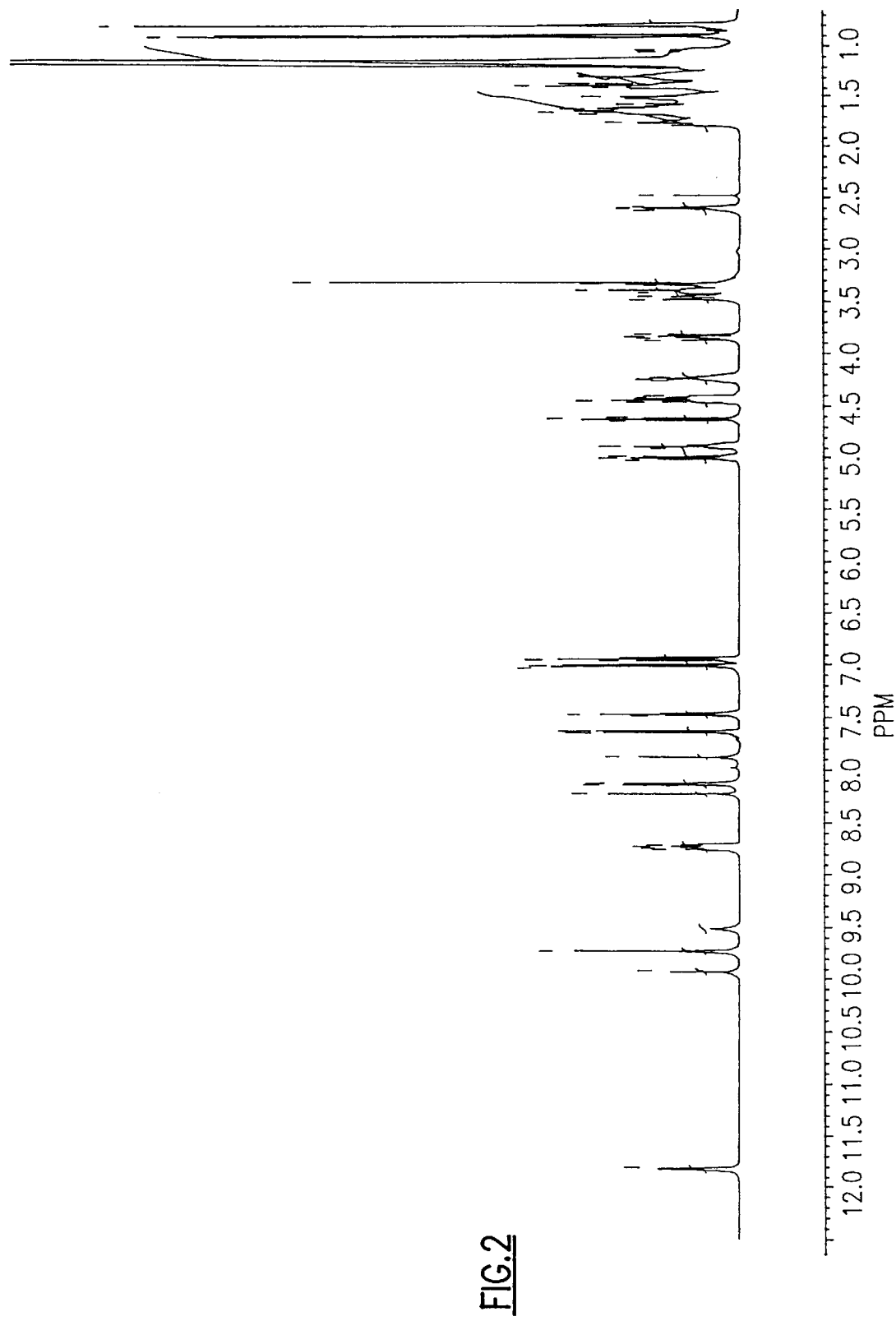
FIG. 2 shows the $^1$H-NMR spectrum of BMS-199687 (500 MHz in DMSO-$d_6$).
Figure 3:
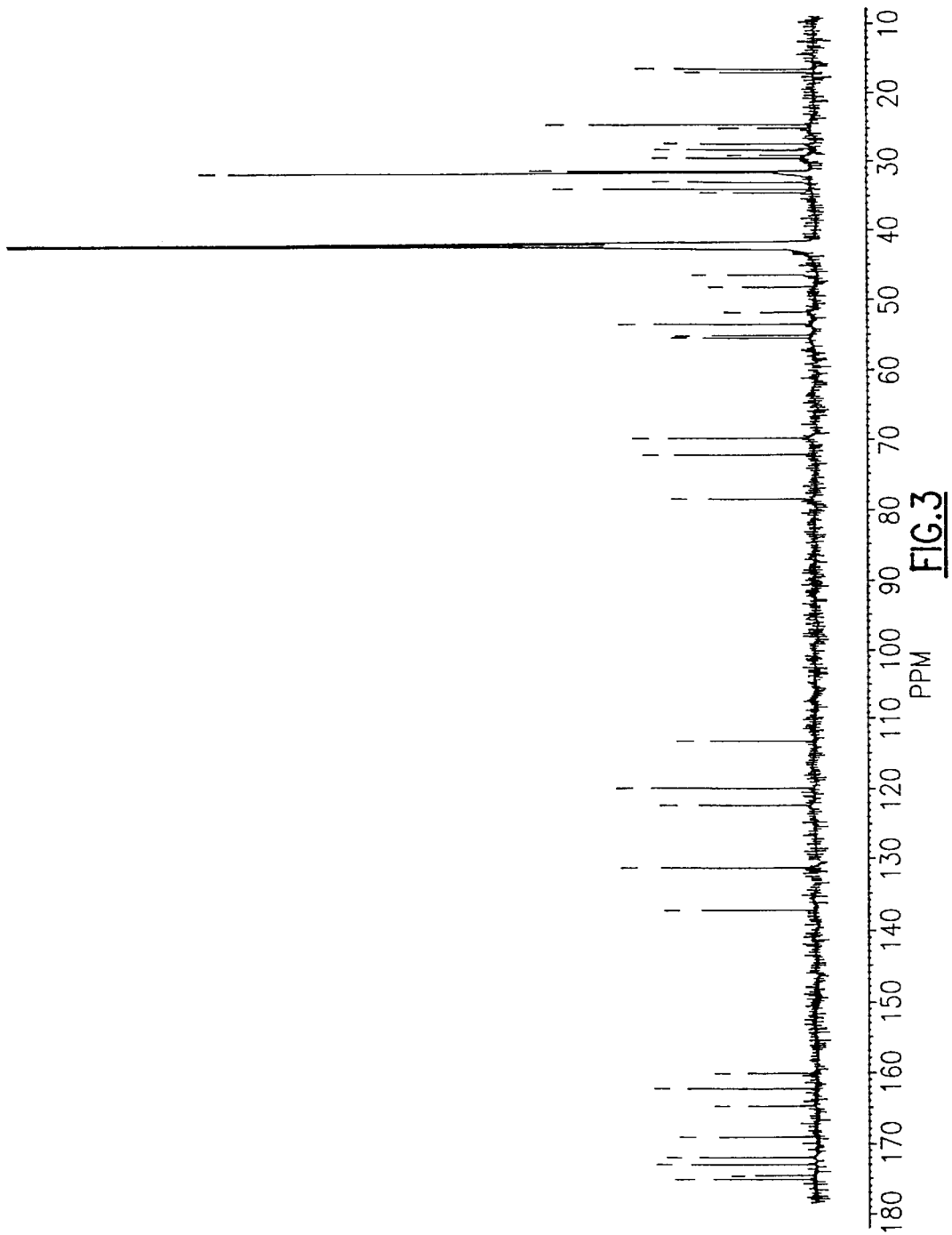
FIG. 3 shows the $^{13}$C-NMR spectrum of BMS-199687 (125 MHz, DMSO-$d_6$).

This invention relates to a novel antitumor antibiotic designated BMS-199687, said antibiotic being produced by cultivating a BMS-199687-producing strain of *Actinomadura ferruginea*, most preferably *Actinomadura ferruginea* strain WC57581 (ATCC-55733) or a mutant or variant thereof, in an aqueous nutrient medium containing assimilable sources of carbon and nitrogen under submerged aerobic conditions until a substantial amount of BMS-199687 is produced by said organism in said culture medium. The BMS-199687 so-produced may be isolated from the fermentation medium in substantially pure form by conventional procedures. BMS-199687 exhibits antitumor activity in standard antitumor animal model systems.

DETAILED DESCRIPTION OF THE INVENTION

The BMS-199687 antibiotic of the present invention may be obtained by fermentation of a BMS-199687-producing strain of *Actinomadura ferruginea*. The preferred producing organism is a novel strain of *Actinomadura ferruginea* designated herein as *Actinomadura ferruginea* WC 57581. This organism was obtained from a soil sample collected in Utter Pradesh, India. A biologically pure culture of strain WC 57581 has been deposited with the American Type Culture Collection (ATCC), Rockville, Md., USA and added to its permanent collection of microorganisms as ATCC-55733. The culture is also maintained as a dormant culture in lyophile tubes and cryogenic vials in the Bristol-Myers Squibb Pharmaceutical Research Institute Culture Collection, 5 Research Parkway, Wallingford, Conn. 06492, USA.

The results of taxonomic studies performed on strain WC 57581 indicate that the strain is a novel strain of Actinomadura. Based on its characteristics, as indicated below, strain WC 57581 is believed to belong to the species group *Actinomadura ferruginea*.

Growth of strain WC 57581 on solid media showed a dense non-fragmented orange substrate mycelium with aerial mycelium moderately developed—white to very pale pink depending on the growth medium. Mature aerial mycelium formed short spore chains, mostly straight and hooked. Growth on Yeast Extract-Malt Extract Agar (ISP-2) showed a brown-red soluble pigment with no fragmentation of the mycelium. The reverse is yellow-orange. Coremia are present on a rudimentary aerial mycelium. The aerial mycelium has short sporophores with spores in straight and hooked chains. Growth on Oatmeal Agar (ISP-3) is abundant with no soluble pigments, no reverse colors and no fragmentation of the mycelium. The substrate mycelium is orange with no fragmentation; the aerial mycelium is white with good sporulation on short sporophores. Spore chain are mainly straight and hooked. Growth characteristics on Inorganic salts-Starch Agar (ISP-4) were the same as on Oatmeal Agar.

The cell wall peptidoglycans contain meso 2,6-diaminopimelic acid (meso-DAP) as the principal diamino acid. Whole cell hydrolysate contains glycine and the sugar, madurose. Glucose, rhamnose and fructose are utilized as the sole carbon sources. Based on cell wall composition, this culture is classified as a member of the genus Actinomadura. Based on further data involving spore morphology and the color of substrate mycelium, the organism is classified as a strain of *Actinomadura ferruginea*.

As in the case with other microorganisms, the characteristics of the new producing culture of the present invention, *Actinomadura ferruginea* ATCC-55733, are subject to variation. Recombinants, variants and mutants of the ATCC-55733 strain may be obtained by treatment with various known mutagens such as ultraviolet rays, X-rays, high frequency waves, phage exposure, radioactive rays and chemicals. Natural and induced variants, mutants and recombinants of *Actinomadura ferruginea* ATCC-55733 which retain the characteristic of producing BMS-199687 are intended to be encompassed by the present invention.

The antibiotic BMS-199687 of the present invention may be produced by cultivating a BMS-199687-producing strain of *Actinomadura ferruginea*, preferably a strain having the identifying characteristics of strain WC 57581 or a variant or mutant thereof, in a conventional aqueous nutrient medium. The organism is grown in a nutrient medium containing known nutritional sources for actinomycetes, i.e. assimilable sources of carbon and nitrogen plus optional inorganic salts and other known growth factors, Submerged aerobic conditions are preferably employed for the production of large quantities of the antibiotic, although for production of limited amounts surface cultures and bottles may also be used. The general procedures used for cultivation of other actinomycetes are applicable to the present invention.

To elaborate on preferred cultivation conditions, the organism is grown in a nutrient medium containing an assimilable source of carbon such as glucose, cellobiose, trehalose, potato starch, glycerol or ribose. The medium should also contain an assimilable source of nitrogen such as fishmeal, peptone, peanut meal, cottonseed meal or cornsteep liquor. Nutrient inorganic salts can also be incorporated in the medium so as to provide sodium, potassium, ammonium, calcium, phosphate, nitrate, chloride, bromide, carbonate, and like ions. Trace elements such as copper, manganese, iron, zinc, etc. are added to the medium if desired, or they may be present as impurities of other constituents of the medium.

Production of BMS-199687 can be effected at any temperature conducive to satisfactory growth of the producing organism, e.g 22° to 42° C., and is conveniently carried out at a temperature of about 28° C. The fermentation may be carried out in shake flasks or in laboratory or industrial fermentors of various capacity. When tank fermentation is to be used it is desirable to produce a vegetative inoculum in a nutrient broth by inoculating a small volume of the culture medium with a slant, a cryopreservative culture or a lyophilized culture of the producing organism. After obtaining a viable and active inoculum in this manner, it is transferred aseptically to the fermentation tank charged with production medium for large scale production of BMS-199687. The medium in which the vegetative inoculum is prepared can be the same as or different from that used in the tank as long as it is such that a good growth of the producing organism is obtained. Further agitation may be provided by a mechanical impeller. Antifoam agents such as lard oil or silicone oil may also be added if needed. Antibiotic production may be monitored by high performance liquid chromatography (HPLC) assay or by conventional biological assay. When the fermentation is complete, the BMS-199687 antibiotic is extracted from the culture broth with a suitable organic solvent and the antibiotic recovered from the extract and purified by conventional isolation procedures such as those described in the examples below.

Physico-Chemical Properties

A purified sample of BMS-199687 was isolated as a white amorphous powder. The antibiotic is readily soluble in dimethyl sulfoxide (DMSO) and chloroform, slightly soluble in methanol and practically insoluble in water. It gave a positive response to ferric chloride and Rydon-Smith reagents but was negative to ninhydrin and Sagakuchi tests. The molecular formula was determined to be $C_{40}H_{63}N_5O_{10}$. Other characterizing properties are shown below in Table I.

TABLE 1

Physico-chemical properties of BMS-199687

| Appearance | White amorphous powder |
| --- | --- |
| Melting point | 145° C. |
| $[\alpha]_D^{25}$ | −11° (c 1.0, $CHCl_3$) |

TABLE 1-continued

Physico-chemical properties of BMS-199687

| Molecular formula | $C_{40}H_{63}N_5O_{10}$ |
| --- | --- |
| Molecular weight | 773 |
| LR-MS (m/z) | 774 $(M + H)^+$ |
| HRFAB-MS (m/z) | |
| Observed | 773.4546 |
| Calculated | 773.4574 |
| UVλmax nm$^{(E1\%1cm)}$ in $CH_3OH$ | 210 (570), 242 (158), 249 (162), 258 (sh 88), 305 (72) |
| in 0.1N HCl—$CH_3OH$ | 209 (512), 256 (257), 330 (83) |
| in 0.1N NaOH—$CH_3OH$ | 223 (521), 248 (sl.sh 223), 336 (93) |
| IR ν max (KBr) cm$^{-1}$ | 3416, 3322, 2926, 2854, 1736, 1662 (sh), 1640, 1540, 1492, 1376, 1368 1260, 1231, 756 |
| TLC, $SiO_2$ ($CHCl_3$—$CH_3OH$ = 9:1) | Rf 0.29 |
| HPLC (YMC-Pack A301-3, $CH_3CN$ - 0.15% $KH_2PO_4$ buffer, pH 3.5 = 72:28) | Rt 8.0 min. |

Based on the physico-chemical properties of BMS-199687, the structure was determined to be as shown below:

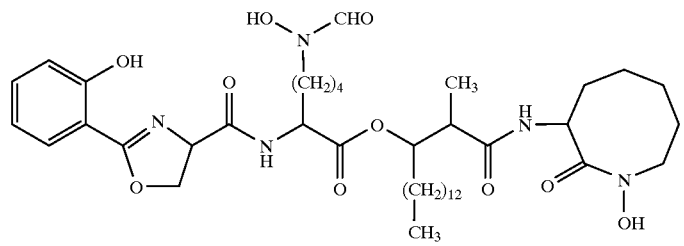

Biological Properties

BMS-199687 was evaluated in vitro on a murine cell line M109 (Madison lung carcinoma 109) for cytotoxic activity. This cell line was derived from an in vivo grown tumor (Bursuker, I et al, *J. Interf. Res.* 10:1–11, 1990) and was propagated in vitro in 175 ml Falcon tissue culture flasks in culture medium consisting of Dulbecco's modified Eagle's medium (DMEM) supplemented with 10% Fetal Bovine serum (FBS) and antibiotics. The test procedure is as follows:

For the assay the cells were removed from the flask with a 0.25% solution of trypsin in Hank's Balanced Salt Solution (Life Technologies, Grand Island, N.Y.) and washed in culture medium. A viable cell count assessed using a 0.4% solution of Typan Blue (Life Technologies). The cells were then plated onto 96 well microtiter plates, $1 \times 10^4$ cells/well in a volume of 180 μl. The plates were incubated in $CO_2$ incubators at 37° C. for 3 hours to allow the cells to adhere. The compound was then added to the well at desired concentrations in a volume of 20 μl and incubated for 48 hours. Wells with no compound added served as a control. At the end of the incubation period, the viable cells were quantitated using the Neutral Red staining procedure (Borenfreund, J. et al, *J. Tissue Cult. Meth.* 9:7–9, 1984). Briefly the cells were incubated for two hours with a 40 μg/ml solution of neutral red, fixed for ten minutes with a 3% solution of formaldehyde and thoroughly washed with PBS (Bio Whittaker). The dye was then eluted from the cells by incubating them for 15 minutes at room temperature with a solution of 50% ethanol and 1% acetic acid. Dye absorbance was measured at 550 nm using Thermomax Microplate Reader (Molecular Devices, Sunnyville, Calif.). The cytotoxic activity was calculated using the following formula:

$$\text{cytotoxic activity} = \left(1 - \frac{\text{O.D. Sample} - \text{O.D. blank}}{\text{O.D. Control} - \text{O.D. blank}}\right) \times 100\%$$

Figure 4:
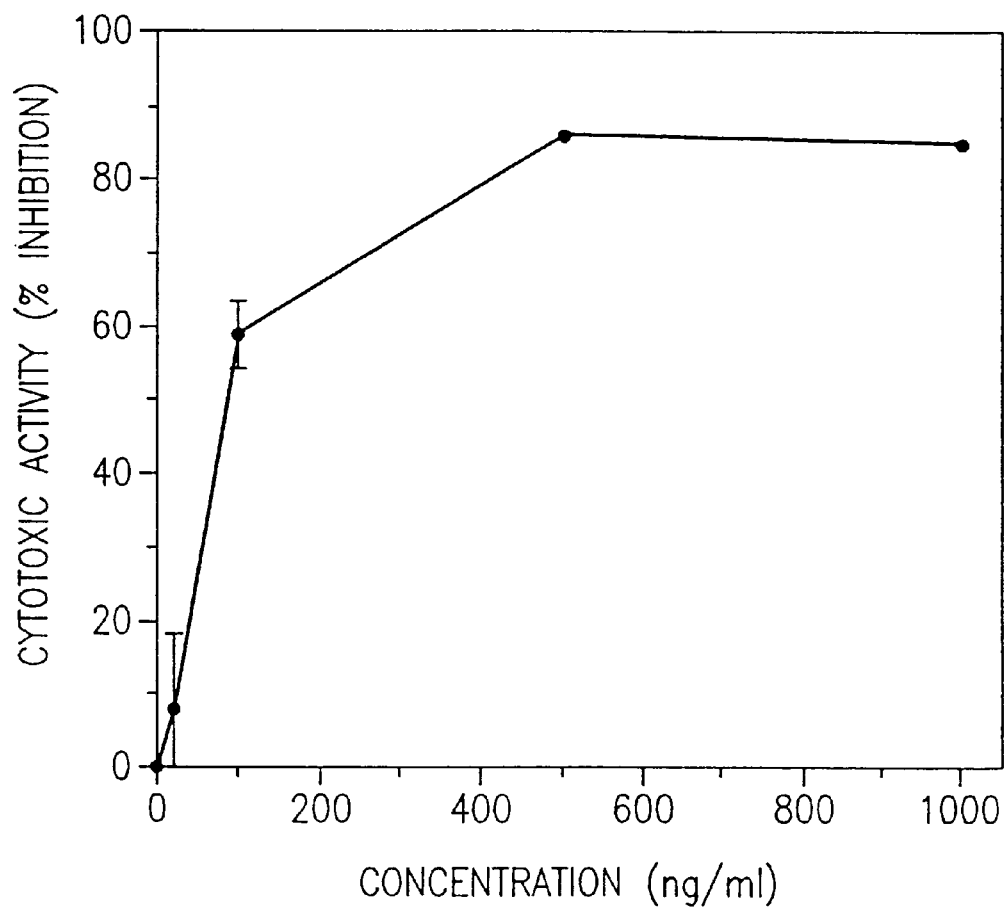
FIG. 4 shows the cytotoxic activity of BMS-199687 when evaluated in vitro on murine cell line M109.

The cytotoxic activity of BMS-199687 is shown in FIG. 4.

BMS-199687 was also tested in vivo in the M109 (Madison Lung Carcinoma) model as described by W. Rose in *Cancer Treatment Reports*, 65: No. 3–4, pp. 299–312, 1981. The test procedure is as follows: Balb/cxDBA/2 (CDF1) hybrid mice were implanted intraperitoneally(ip) with 0.5 ml of a 2% (w/v) brei of M109 lung carcinoma as described by W. Rose in the above-quoted reference. BMS-199687 and reference drug, olivomycin A, were administered ip to groups of mice. Each group received a compound at a different dose level, four different dose levels of BMS-199687 were evaluated; each dose was administered once daily for five consecutive days beginning one day after tumor implantation. Mice were followed daily for survival until their death or about 100 days post implant, whichever occurred first. One group of mice remained untreated and served as the control. Median survival times of BMS-199687 treated (T) mice were compared to the median survival time of the parallel control (C) mice. The ratio of the two values of each compound treated group of mice was multiplied by 100 and expressed as a percentage (i.e., %T/C). A compound showing %T/C higher or equal to 125% is considered active in this tumor model. BMS-199687 when given ip according to the above-specified protocol in the dose range of 1 to 30 mg/kg per injection once daily for five days produces T/C values between 100% and 143%. BMS-199687 is therefore an effective tumor-inhibiting agent.

Therapeutic Use

As indicated above BMS-199687 has been found to possess both in vitro and in vivo antitumor activity in standard antitumor tests. In one aspect, then, the present invention provides a method of treating a mammalian host affected by a malignant tumor sensitive to BMS-199687 which comprises administering to said host a tumor-inhibiting dose of BMS-199687 or a pharmaceutical composition thereof.

In another aspect the present invention provides pharmaceutical compositions comprising an effective tumor-inhibiting amount of BMS-199687 in combination with an inert pharmaceutically acceptable carrier or diluent. Such compositions may contain other antitumor agents and may be made up in any form appropriate for the desired route of administration. Examples of such compositions include solid compositions for oral administration such as tablets, pills, capsules, powders and granules; liquid compositions such as solutions, suspensions or syrups, and preparations for parenteral administration such as sterile solutions, suspensions and emulsions. They may be also manufactured in the form of sterile solid compositions which can be dissolved in sterile water, physiological saline or some other sterile injectable medium just before use.

Optimal dosage and regimen of BMS 199687 for a given mammalian host can be readily ascertained by those skilled in the art. It will be appreciated, of course, that the actual dose of compound used will vary according to the particular composition formulated, the mode of application and the particular situs, host and disease being treated. Many factors that modify the action of the drug will be taken into account, including age, weight, sex, diet, time of administration, route of administration, rate of excretion, condition of the patient, drug combinations, reaction sensitivities and severity of the disease.

The following examples are provided for illustrative purposes only' and are not intended to limit the scope of the invention.

EXAMPLE 1

Preparation of vegetative culture of *Actinomadura ferruginea* WC-57581

A vegetative culture was prepared by transferring 4 ml of the cryopreserved culture to a 500 ml Erlenmeyer flask containing 100 ml of sterile vegetative medium V13 having the following composition: 2% soluble starch, 0.5% glucose, 0.3 NZ-case, 0.2% yeast extract, 0.5% fish meat extract and 0.3% calcium carbonate. The vegetative culture was incubated at 32° C. and 250 revolutions per minute (rpm) on a rotary shaker for 72 hours.

EXAMPLE 2

Fermentation of BMS 199687

Four ml of the vegetative culture as produced above were transferred to a 500 ml Erlenmeyer flask containing 100 ml of production medium F1A. Production medium F1A was prepared using 2% soluble starch, 1% glucose, 1% Pharmamedia, 0.3% NZ-Amine A and 0.3% calcium carbonate. The production culture was incubated for 4 to 6 days at 28° C. and 250 rpm on a rotary shaker. The production of BMS-199687 reached a maximum of 50 ug/ml at day 5 in the cycle.

EXAMPLE 3

Isolation and Purification of BMS-199687

Whole broth (10 liters) as provided according to Example 2 above was stirred vigorously with n-butanol (6 liters) for one hour. The phases were separated and the organic extract concentrated in vacuo to an aqueous solution (500 ml) which was extracted twice with ethyl acetate (300 ml each). The organic layer was evaporated to dryness and the residue partitioned between n-hexane and 90% aqueous methanol (1:1, 600 ml) mixture. The methanol layer was concentrated to give a crude material of BMS-199687(5.39 g). The crude solid was dissolved in chloroform(40 ml) and charged to a silica gel column (Silica Gel 60, Merck, 600 ml) which was developed with ethyl acetate-methanol (10:1), 1.5 liters), followed by methanol (1 liter) and chloroform-methanol water (4:7:2, 1.3 liters). The eluate was collected in fractions of 200 ml and each fraction monitored by the cytotoxic activity on M109 murine cell line and TLC (Silica Gel 60 F254, Merck, Chloroform-Methanol 9:1). The active eluates obtained from the chloroform-methanol-water elution were concentrated under vacuum yielding a semi-pure solid(723 mg). The material was dissolved in DMSO(10 ml) and applied to a column of reverse phase C18 (YMC GEL, BS-5005, YMC Co.,LTD., 900 ml). The column was washed with acetonitrile-0.15% $KH_2PO_4$, pH 3.5(80:20,2 liters). Active effluates were concentrated to an aqueous solution which was washed with water and evaporated under reduced pressure to yield an analytically pure sample of BMS-199687.

We claim:

1. A process for the preparation of BMS-199687 having the formula

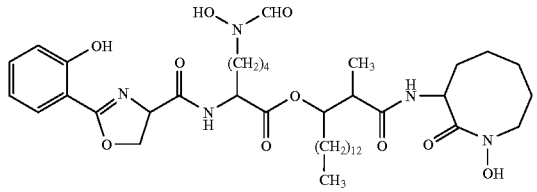

which comprises cultivating a BMS-199687-producing strain of *Actinomadura ferruginea* in an aqueous nutrient medium containing assimilable sources of carbon and nitrogen under submerged aerobic conditions until a substantial amount of BMS-199687 is produced by said organism in such culture medium and then recovering said BMS-199687 from the culture medium.

2. The process according to claim 1 wherein the BMS-199687-producing strain is *Actinomadura ferruginea* strain WC57581 (ATCC-55733) or a variant or mutant thereof.

3. A biologically pure culture of the microorganism *Actinomadura ferruginea* strain WC57581 (ATCC-55733) which is capable of producing the antibiotic BMS-199687 of the formula

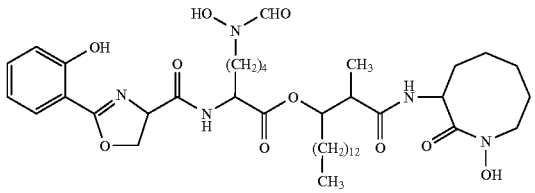

in a recoverable quantity upon cultivation in a culture medium containing assimilable sources of carbon and nitrogen under submerged aerobic conditions.

* * * * *